(12) United States Patent
Dunkelberg

(10) Patent No.: US 8,541,195 B2
(45) Date of Patent: Sep. 24, 2013

(54) METHOD FOR TESTING A STERILIZATION PACKAGING UNIT

(76) Inventor: Hartmut Dunkelberg, Bad Sooden-Allendorf (DE)

( * ) Notice: Subject to any disclaimer, the term of this patent is extended or adjusted under 35 U.S.C. 154(b) by 485 days.

(21) Appl. No.: 13/012,083

(22) Filed: Jan. 24, 2011

(65) Prior Publication Data

US 2011/0117595 A1 May 19, 2011

Related U.S. Application Data

(62) Division of application No. 10/556,550, filed as application No. PCT/EP03/05111 on May 15, 2003, now Pat. No. 7,874,128.

(51) Int. Cl.
*C12Q 1/22* (2006.01)
*B65B 55/02* (2006.01)
*G01N 31/00* (2006.01)

(52) U.S. Cl.
USPC .................................. 435/31; 53/425; 436/1

(58) Field of Classification Search
USPC .................................. 435/31; 53/425; 436/1
See application file for complete search history.

(56) References Cited

U.S. PATENT DOCUMENTS

| | | | |
|---|---|---|---|
| 4,596,773 A | 6/1986 | Wheeler, Jr. | |
| 4,717,661 A | 1/1988 | McCormick et al. | |
| 4,743,537 A | 5/1988 | McCormick et al. | |
| 4,925,789 A | 5/1990 | Edberg | |
| 5,167,923 A | 12/1992 | Van Iperen | |
| 5,344,017 A | 9/1994 | Wittrock | |
| 5,863,496 A | 1/1999 | McElhany | |
| 5,922,592 A | 7/1999 | Tautvydas | |
| 5,955,296 A | 9/1999 | Roll | |
| 6,770,454 B2 | 8/2004 | Reilly et al. | |
| 2002/0022246 A1 | 2/2002 | Lin et al. | |
| 2005/0191750 A1 | 9/2005 | Dunkelberg | |

FOREIGN PATENT DOCUMENTS

| | | |
|---|---|---|
| DE | 10006767 | 8/2001 |
| DE | 10213361 | 8/2004 |
| GB | 2186974 | 8/1987 |
| WO | 0113964 A1 | 3/2001 |

OTHER PUBLICATIONS

M.J. Akers, Parenteral Quality Control: Sterility, Pyrogen, Particulate and Package Integrity Testing; Second Edition, 1994, Chapter 4, pp. 247-299.
BD BBL, Prepared Sterile Pack Plates Trypticase Soy Agar, Sterile Pack, Feb. 2000, http://www.bd.com/ds/technicalCenter/inserts/8809381(0200).pdf; downloaded Feb. 1, 2011.
European Standard, EN 556-1, Sterilization of Medical Devices—Requirements for Medical Devices to be Designated 'Sterile', pp. 1-6, Oct. 2001.
3M Media, 1 page, no date.
Gke-Bio-Plus-Indikatoren, Bio-Plus-D/Stand9-99, 2 pages, Sep. 1999.
American Society for Testing Materials (ASTM), Lizenzierter Nachdruck, Standard Guide for Design and Evaluation of Primary Packaging for Medical Products, Designation: F 2097-01, pp. 1-11, Dec. 2001.
H. Dunkelberg, S. Wedekind, Rekontamination von Papierver-Packten Sterilgutpacketen unter Mechanischer Belastung, pp. 1 and 29, Hyg Med 27, Apr. 2002.
Harmut Dunkelberg, MD, Bjorn Zietz, MD and Silke Wedekind, Preliminary Results for a New Final Package Test to Assess the Quality of Sterile Package Systems; The Society for Healthcar Epidemiology of America 13th Annual Scientific Meeting, Meeting Information; pp. 1 and 101, Section 214, Monday, Apr. 7, 2003.
Dunkelberg et al., A New Method for Testing the Effectiveness of the Microbial Barrier Properties of Packaging Materials, Biomedizinische Technik, vol. 47 (11) (2002) pp. 290-293 (English Translation).
Bruijin et al., Single or Multiple Wrapping of Medical Devices: Procedure Assessment Through Research, Zentr 7. Jahrgang, 1999; pp. 292-303.
Junghannss et al., Hygienic-Microbiological and Technical Testing of Steriliser Container Systems, Zentr Steril 7. Jahrgang, 1999, pp. 154-162.
EN 868-1; Verpackungsmaterialien und-systeme fur zu sterilisierende Medizinprodukte Europaische Norm European Standard Norme Europeenne, Feb. 1997, pp. 1-12.
DIN 58-953; Sterilgutversorgung; Sterilisationpapier fur Beuter und Schlauchverpackungen Prufung Sterilization; Sterile Supply; Sterilization Paper for Bags and Tube Packings, test, Jan. 1987, pp. 1-3.
Aesculap; Sterile Containers; Instructions for Use/ Technical Description, Dec. 1997, pp. 1-4.
American Society for Testing and Materials F 1608-00; Standard Test Method for Microbial Ranking of Porous Packaging Materials (Exposure Chamber Method), pp. 1-9, Jun. 2000.
Aesculap, Basic Version of Sterile Containers; B. Braun Melsungen AG, http://www.bbraun.com/Index.cfr?uuld=97E644D8B349489E89; Apr. 11, 2004; one sheet.
BD BBL, BD Best Practive Formulary, BD BBL™ Prepared Plated Media; BD BBL™ Product Insert (2002), pp. 1-39.
Patent Cooperation Treaty PCT International Preliminary Examination Report for International Patent Application PCT/EP2003/005111; Aug. 26, 2005, pp. 1-6 (English Translation).
Marti, P, PCT International Search Report for International Application No. PCT/EP03/05111; Oct. 13, 2003; pp. 1-3.

*Primary Examiner* — Susan Hanley
*Assistant Examiner* — Paul Martin
(74) *Attorney, Agent, or Firm* — Ballard Spahr LLP

(57) ABSTRACT

A testing unit and a method of testing a sterilization packaging unit for microbial contamination of sterilized objects after they have been sterilized are disclosed. The testing unit includes a dry matrix for accommodating a nutrient medium and a receptacle containing a liquid. By applying the liquid onto the matrix, the matrix is provided with a nutrient medium. In the method, the testing unit is inserted into the sterilization packaging unit which is sterilized and stored. At a desired point in time, the receptacle is opened in order to produce the nutrient medium in the matrix. After a possible multiplication of microbes on the matrix, an observation of microbes takes place. The invention also relates to a sterilization packaging unit which has a rigid outer casing and is suitable for the application of the method.

5 Claims, 2 Drawing Sheets

METHOD FOR TESTING A STERILIZATION PACKAGING UNIT

CROSS REFERENCE TO RELATED APPLICATIONS

This application is a Divisional application based on U.S. patent application Ser. No. 10/556,550, filed Nov. 27, 2006, which issued as U.S. Pat. No. 7,874,128, on Jan. 25, 2011, which in turn is a National Stage Application of International Patent Application No. PCT/EP03/05111, filed May 15, 2003, the disclosures of which are incorporated herein by reference.

FIELD OF THE INVENTION

The invention relates to a testing unit and a method for testing a sterilization packaging unit which is provided for the sterilization of objects to be sterilized, in particular medical objects to be sterilized, with regard to the efficacy of the sterilization packaging unit in preventing microbial recontamination of the sterilized objects after they have been sterilized. The invention also relates to a particular sterilization packaging unit, namely one which comprises at least partially a rigid outer casing. The sterilization packaging unit last referred to renders it possible to apply the method of testing the efficacy against recontamination also to this type of sterilization packaging unit.

BACKGROUND OF THE INVENTION

The term sterilization packaging unit refers to the package per se, i.e. without any content. For example, a sterilization packaging unit can be a so-called primary package which is a sealed or closed packaging system for enclosing the objects to be sterilized. The term packaging system refers to one or several packaging materials which are intended as part of or all of a primary package. The sterilization packaging unit can also be a so-called secondary package which is provided to accommodate one or several parts of objects to be sterilized, each one contained in its primary package. The term sterilization packaging unit is intended to refer in particular to an end-usage package. This relates to the package, in which in particular a medical product is sterilized. The end-usage package can be a primary package which is additionally provided with a secondary and/or transport package.

Many objects must be sterilized before they are used, particularly in the medical field, in order to kill microbes, i.e. viable microorganisms, on the objects. Such medical objects to be sterilized can be, for example, instruments, linen or liquids. Depending on the type of objects to be sterilized an appropriate physical or chemical sterilization method is used. In the medical field vapor sterilization methods are predominantly used. These are characterized by a high level of efficacy and environmental compatibility. In vapor sterilization methods sterilization is carried out with confined and saturated steam. The temperature of the steam is for example 121° C. or 134° C. Sterilization is carried out using autoclaves.

Furthermore, microbes can also be killed by high-energy ionizing beams or by an H2O2-based plasma. Chemical sterilization methods include sterilization by means of ethylene oxide or formaldehyde.

Medical objects to be sterilized are packaged for sterilization. It is possible for this purpose to use container packages, e.g. in the form of a box, paper packages in which the objects to be sterilized are wrapped in a number of layers of paper, and other packages. Paper packages which have a transparent casing are used in industry to pack sterile disposable material and in hospitals for individually packing disposable material or reusable goods. These packages can be in particular packages based upon transparent bags and transparent tubes consisting of paper and synthetic composite sheeting. The package serves to ensure the sterility achieved by the sterilization method until the sterilized objects are used. They can be stored in hospitals for a period of weeks to several months.

The quality requirements for the sterilization method are high. Under WHO guidelines and various European pharmacopoeia, out of 1000000 "sterile" products 999999 must be sterile. This requirement forms the substantial content of the European Standard EN 556-1:2001.

The sterilization method itself is typically evaluated and standardized with physical-chemical and microbiological parameters. A known and reliable method for testing the efficacy of a sterilization method consists of subjecting a test microbial unit to the sterilization method to be tested, at the same time as the objects to be sterilized. This test microbial unit is formed by a number of microbes which are particularly resistant to the sterilization process and which are enclosed as a unit by a casing. After the sterilization process this test microbial unit is opened under sterile conditions and tested to see if the microbes contained therein are capable of multiplying. If the sterilization process has taken place correctly no multiplication of the test microbes will take place since these test microbes have been killed by the sterilization. The test microbes therefore represent an indicator for the effectiveness of the sterilization method.

A test microbial unit of this type is provided in particular in the form of self-developing bio-indicators (available from the company 3M Medica, branch of 3M Deutschland GmbH, Neuss, Germany). They comprise an ampoule, containing nutrient medium, and a plastic casing, in which the ampoule and spores of a defined microbe type are located. The plastic casing comprises a closure having a vapor-permeable, but microbe-tight filter. The bio-indicators are subjected to the sterilization process which is to be tested. The ampoule is then crushed. As a consequence, the microbes and the nutrient medium are mixed together. The indicator is then incubated in the incubator and is evaluated in terms of a change in color of the nutrient medium. If there is no change in color, no microbial growth has taken place. In this case, the sterilization method has been efficient and has killed the microbes of the bio-indicator. A similar indicator is also available from the company gke-mbH, Waldems-Esch, Neuss, Germany. However, the design of indicators of this type means that they cannot be used to test whether, after successful sterilization, any recontamination of the sterilized objects has occurred during a specific period of storage.

There are also quality standards for the packaging material. These generally relate to partial aspects of the sterilization packaging unit such as material properties, sealing tightness of closures etc.

On the one hand, the so-called microbial barrier of the sterilization packaging unit used is a factor in the recontamination of the sterilized objects. This microbial barrier is the ability of the sterilization packaging unit to prevent the entry of microorganisms. On the other hand, various external influences such as the type of storage or transportation and mechanical stressing on the packaged sterilized objects and ambient influences such as air flow, microbial content of the air and fluctuations in air pressure are factors in recontamination.

A known device for testing the microbial barrier quality of partial components of a container package is formed in such a manner that it generates a negative pressure in one container via orifices provided in a cover of the container (EN 868-1, Appendix G). By means of this negative pressure the tightness of a seal between the cover and the container body can be tested. However, this is merely a device for a specific physical testing method for packages which are in the form of containers. This method relates merely to the seal between the body and the cover but not the microbial barrier of the vapor orifices such as filters and valves. Furthermore, ambient influences, e.g. microbial content of the air, are not included in this testing method. This device can therefore give no reliable evidence as to the extent to which recontamination of sterilized objects in the sterilization packaging unit must be expected.

Furthermore, there is a microbiological DIN testing device (DIN 58953, Part 6) which is provided to test sterilization paper. In this device a microbial penetration testing unit in the form of a glass laboratory flask is closed with the sterilization paper to be tested and is tested to see whether, by cooling the air in the microbial penetration unit, an air flow passes into the glass laboratory flask and carries particles containing microbes through the sterilization paper when the paper has been coated with a powder containing a defined microbe count of Bacillus-subtilis spores prior to cooling. Provision is made to heat the glass laboratory flask to 50° C. and to cool it to 10° C. repeatedly and consecutively. Spores which may enter the glass laboratory flask through the sterilization paper are observed and evaluated by microbiological means using incubation of the glass laboratory flask containing nutrient medium. This testing method, however, does not relate to a sterilization packaging unit as a whole but only to paper which is used as a packaging material. This is purely a material test in which, apart from the application of the powder, no further ambient influences are included.

From the publication by de Bruijn, A.C.P. and Kastelein, J., Einfach-oder Mehrfach-Verpackung von Medizinprodukten: Verfahrensbewertung durch Forschung, Zentralsterilisation; 1999; 7 (5): 292-303 a device is known with which the filtering effect of a package with respect to an aerosol consisting of 1.0•m latex particles is determined by means of a particle counter (cf. loc, cit., 3., page 297, para. 1). The known method is not intended, and is not suitable for testing packages in the form in which they are used in order to determine their capability to maintain sterility under hospital practice conditions. In particular, the method forming the basis of the device is not based on the determination of the relevant end point, namely the detection of microbiological contamination.

From the American Society for Testing and Materials (ASTM) designation F 1608-00 describes a method which serves to determine the microbial penetration or barrier efficacy of porous materials such as paper: a microbe-containing aerosol including *Bacillus subtilis*-spores is introduced into a chamber by means of an atomizer. By the intermediate placement of the test material on to filter carriers and a further microbe-tight filter membrane, it is possible to determine the microbial penetration of the test body during a defined passage of a microbe-containing aerosol. In this case, it is a device for testing material used for packaging purposes but not a device for examining a sterilization packaging unit which is typically used in practice.

It is also known to test some of the sterilized objects for recontamination after a certain period of time by means of random sampling. However, a disadvantage of this is the fact that to do this the sterilization packaging unit needs to be opened and, during the test itself, microbes can reach the object being tested so that the result of the test can thereby be rendered erroneous. However, this method is not practicable for hospital use so that it is not routinely used in hospitals.

From the publication by Junghannβ U., Winterfeld S., Gabele L., Kulow U., Hygienisch-mikrobiologische and technische Überprüfungen von Sterilisier-Containersystemen, Zentralsterilisation 1999; 7 (3): 154-162 a device is known for testing sterilization containers in the form of packaging containers. This device consists of a test chamber, into which the containers to be tested can be inserted. Before they are placed in the test chamber the containers were fitted with the associated filters and sterilized. The containers were then provided with solid nutrient medium in Petri dishes and closed. A microbe-containing aerosol was introduced into the interior of the test chamber using a spray bottle. By means of a connection fitting fitted to the containers to be tested prior to introduction into the test chamber, suction was carried out through the containers to be tested, by means of a hose pump. After the suction the containers were opened again and the solid nutrient medium dishes were removed. These were then incubated to test for microbes on the solid nutrient medium. The colony-forming units (cfu) were then counted.

The known device is not suited to testing an end-usage package in the form in which it is used in practice, in order to test its barrier efficacy with respect to recontamination. It is rather the case that the containers need to be provided with a suction fitting before being introduced into the known test chamber. Furthermore, after the containers have been in contact with the aerosol in the test chamber, they must be removed from the test chamber and opened in order to remove the solid nutrient medium dishes and to incubate them in a separate apparatus. The container cannot therefore remain in an undisturbed condition until the results of the test are evaluated. External sources of errors can therefore not be ruled out during the test. It is rather the case that the removal of the solid nutrient medium dishes for subsequent incubation is associated with a risk of contamination and therefore with the risk of imprecise measurement. According to Junghannβ et al. only a difference value for the microbial barrier is determined but no absolute value is obtained. In the known testing arrangement no evidence as to sterility could be obtained because of the non-sterile handling of the solid nutrient medium.

In the European Standard EN 868-1 of 1997 it is stated under point 4.6 that there was no suitable end-usage package testing method which is standardized. Also there is still no such method in place at the present time. Therefore, in "ASTM-Standard Guide for Design and Evaluation of Primary Packaging for Medical Products" of 2001 (Designation: F 2097-01) it is noted under point 4.6.2 that no individual testing method could completely predict the efficiency of the end-usage package.

To date, only one method has been proposed which is suitable for testing the packaging as a whole or a sterilization packaging unit in use, for its efficacy in preventing recontamination of the sterilized objects in the period of time between sterilization and usage thereof (Dunkelberg, H. und Wedekind, S., Hygiene+Medizin, 27th year, 2002-Suppl. 1, 29 Rekontamination von papierverpackten Sterilgutpaketen unter mechanischer Belastung; Dunkelberg, H. und Wedekind, S., Biomedezinische Technik, 47 (2002), 290-293, Eine neue Methode zur Wirksamkeitsprüfung von Sterilisiergutverpackungen in der Praxis). Using this method which is the subject of the pending German patent application 102 13 361.1, it is also possible to detect any recontamination of the sterilized objects which has possibly taken place. In the case of this known method of testing a sterilization packaging unit provided for the sterilization of objects to be sterilized, in particular medical objects to be sterilized, for its efficacy in preventing microbial recontamination of the sterilized objects after they have been sterilized, the following steps are provided: The sterilization packaging unit is charged with nutrient medium, e.g. nutrient agar-filled dishes. The sterilization packaging is then subjected to a sterilization process and subsequently is stored for a period of time under ambient conditions, wherein immediately after the sterilization process it is fundamentally possible that microbes will become established in the nutrient medium. Subsequently, the sterilization packaging unit is subjected to conditions in which microbes multiply for cultivation of microbes which are present in or on the nutrient medium. Finally, the sterilization packaging unit is opened and microbes, which have multiplied in or on the nutrient medium, are observed.

In the case of this known method, the nutrient medium is ready to use immediately after the sterilization process. Even at this point in time, it is possible for microbes to become established and multiply in or on the nutrient medium. The period of time, during which a nutrient medium can be used as a basis for a multiplication of microbes is limited as a result of the unavoidable water loss and amounts to a maximum of two to three weeks e.g. for solid nutrient medium. Therefore, in the case of the known method, the point in time at which effected recontamination can be observed is predetermined to a limited extent by the limited shelf life of the nutrient medium.

Furthermore, a device is known which can be used in particular for carrying out the method in accordance with patent application 102 13 361.1 which is suitable for testing the package as a whole (Dunkelberg, H., Zietz, B., Wedekind, S., The Society for Healthcare Epidemiology of America, 13th Annual Scientific Meeting, Preliminary Results for a New Final Package Test to Assess the Quality of Sterile Package Systems). In this case, the ambient conditions can be fixed such that the sterilization packaging unit to be tested is subjected for a specific period of time to a very high microbial density which does not normally occur in the environment of stored packaging units.

SUMMARY OF THE INVENTION

It is therefore the object of the invention to provide a generic testing unit or a generic testing method, with the aid of which it is possible in a convenient manner to test the end-usage package after typical storage which can amount to weeks or months, without the barrier efficacy of the end-usage package having to be compromised as a result of the testing procedure. It is also the object of the invention to provide a sterilization packaging unit which is suitable for carrying out the method in accordance with the invention even though it comprises at least partially a rigid outer casing.

The object in relation to the testing unit is achieved using a testing unit. The testing unit comprises a matrix unit and a hermetically sealed receptacle containing a liquid. The matrix unit comprises at least one dry matrix to accommodate a nutrient medium or consists exclusively of this dry matrix. A characteristic of the matrix is its capability of binding liquid, i.e. holding it against the force of gravity. Without a corresponding "activation" of the testing unit, the matrix unit also does not contain any complete nutrient medium, i.e. the matrix unit is not yet fully prepared for the growth of possible microbes. On the contrary, this only occurs by virtue of the fact that the liquid is applied on to the matrix. For this procedure which is generally to be performed manually, the receptacle and the matrix unit are connected together in such a manner that as the receptacle is opened the liquid can be brought into contact with the matrix. In general, after the receptacle is opened the liquid will come into contact with the matrix, without further handling of the testing unit being required for this purpose. The receptacle is opened by virtue of a mechanical effect exerted upon the receptacle.

The testing unit is activated by the liquid passing onto the matrix. From this point in time which can be determined by the user, the matrix unit provides a growth base for microbes. It is provided in accordance with the invention that the sterilization packaging unit which is to be tested is not opened in order to activate the testing unit. For example, if the sterilization packaging unit is a paper package, the mechanical effect can be exerted upon the receptacle through the paper package. A corresponding effect can be achieved with a different flexible package. If, after a corresponding evaluation of the matrix unit, it is evident that microbial growth has taken place, e.g. by means of colony formation, it is possible to conclude that at the point in time when the testing unit was activated these microbes were already located in the sterilization packaging unit.

The testing unit in accordance with the invention can thus be used in order to test an end-usage package for possible recontamination of its contents in its conventional state after a period of storage of e.g. two months, wherein the barrier efficacy of the end-usage package does not have to compromised, i.e. there is no risk of recontamination as a result of the testing procedure itself.

The receptacle is preferably an ampoule which can be destroyed by simply crushing it. To this end, it is also preferably provided that the receptacle or the ampoule is surrounded by a plastics casing. An ampoule which is surrounded by a plastics casing is known per se. The plastics casing serves to ensure that when a glass ampoule is manually crushed there is no risk of injury and pieces of glass are captured. Furthermore, the plastics casing can also be used in accordance with the invention to connect the receptacle to the matrix unit. Preferably, means are disposed between the receptacle and the matrix unit which serve to guide the liquid to the matrix. These means can also be provided in a convenient manner by virtue of a corresponding tubular formation of a portion of the plastics casing. A channel or a tube can also be provided, in order to guide the liquid to the matrix.

In particular, the matrix can be a so-called nutrient board. This type of nutrient board which is known per se is a board which in dry form actually contains some or all of the nutrients required for the growth of microbes; but the nutrient board is not ready to use until it is wetted with an appropriate liquid, e.g. water or a physiological saline solution. The dry nutrient board which in particular can be disc-shaped can be kept for a long period of time, e.g. one year.

Alternatively, a liquid, complete nutrient medium can also be contained in the receptacle.

A membrane filter can be disposed on the matrix as a further component of the matrix unit. This type of microbe-tight membrane filter, on which the microbes grow instead of on the matrix is feasible in order to achieve conditions for observing colonies of microbes which are improved over the growth of microbes on the nutrient board. For example, the membrane filter can be secured to the nutrient board by virtue of an adhesive medium or even by means of a bead on the edge of the nutrient board.

The matrix unit is preferably located in a thermostable solid nutrient medium dish.

The matrix unit and the liquid receptacle which is connected thereto can be disposed for the purposes of stabilization on a common carrier consisting of a suitable thermostable material.

In the case of a sterilization packaging unit which comprises completely or in part a rigid outer casing or wall and in particular can be a container package, the receptacle of a testing unit which is positioned in the sterilization packaging unit generally cannot be destroyed by the application of pressure on to the outer casing of the sterilization packaging unit. Therefore, it is provided in accordance with the invention that the sterilization packaging unit comprises, on an inner side of the rigid outer casing, holding means for securing a testing unit. The testing unit comprises a matrix unit having a dry matrix which can bind liquid and is provided for the purpose of accommodating a nutrient medium. Furthermore, the testing unit comprises an hermetically sealed receptacle which is configured and connected to the matrix unit such that by virtue of mechanical effect exerted upon the receptacle, the receptacle can be opened and a liquid contained therein can be brought into contact with the matrix. This type of testing unit has been described above. Furthermore, the sterilization packaging unit comprises at least one actuating means which is attached to the rigid outer casing in such a manner that it extends through the outer casing, wherein the type of attachment is microbe-tight. The actuating means comprises a portion which is used to exert the mechanical effect, which is provided for opening the receptacle of the testing unit, upon the receptacle if a test unit is held by the holding means. To this end, the stop portion within the sterilization packaging unit can be displaced by actuation of the actuating means from the outside when the sterilization packaging unit is not open.

The single or plural actuating means can comprise in particular a threaded bolt. The stop portion is a part of the threaded bolt or is connected thereto, so that by turning the threaded bolt the stop portion can be displaced within the sterilization packaging unit.

In particular, the threaded bolt can be part of a screw. Fundamentally, it is possible to equip packaging units of this type and in particular container packages in the manner described above, in order to fit them as required with a corresponding testing unit and thereby to be able to test them with regard to the efficacy of the sterilization packaging unit against recontamination of the sterilized objects contained in said packages, without having to compromise the barrier efficacy of the sterilization packaging unit for this purpose. The reason for this is that after the receptacle has been opened and the testing unit has been activated, cultivation takes place without the container package being opened beforehand. After usage, the testing unit can be discarded and can be replaced in a convenient manner by a new testing unit. Preferably, the active area of the matrix unit of the testing unit is approximately as large as the base area of the sterilization packaging unit. Of course, it is possible to use other mechanisms for destroying the receptacle of a testing unit which is secured in an at least partially rigid sterilization packaging unit. At the same time, the adjustment position of the screw can provide an indicator as to whether the sterilization packaging unit is fitted with a testing unit.

In the method according to the invention, the aforementioned testing unit is placed into the sterilization packaging unit or, if the sterilization packaging unit is rigid, it is secured therein. The sterilization packaging unit is then subjected to a sterilization process. Then, the sterilization packaging unit is stored for a period of time under ambient conditions. In particular, the ambient conditions and the period of time can be the same as occur in practice. Therefore, in hospitals for example, disposable material such as swabs and compresses or reusable objects are stored for a period of time ranging from weeks to months. However, it is also possible for the ambient conditions to be particular ambient conditions which are provided for the specific testing of the sterilization packaging unit. In particular, they can be conditions which are less favourable with regard to recontamination than is typically the case in practice. After this kind of storage, i.e. at the point in time at which a test is to be performed as to whether recontamination has taken place, the receptacle is opened by means of a mechanical effect and the liquid is brought into contact with the matrix. In the case of a rigid sterilization packaging unit, this can be performed as described above by means of externally accessible actuating means. From this point in time onwards, microbes which are located on the matrix unit are able to grow. To this end, the sterilization packaging unit is subjected to conditions which promote multiplication of microbes, in order to cultivate the microbes present on the matrix unit. The multiplication conditions include e.g. a temperature favorable for the multiplication of the microbes to be expected, and a favorable gas atmosphere. In general, incubation will take place in an incubator. Then, the sterilization packaging unit is opened and microbes which have multiplied in or on the matrix unit are observed. In particular, the number of colonies which have grown on the matrix unit and of which each is attributed to a microbe which initiates them can be determined as a measure of the efficacy of the sterilization packaging unit against recontamination.

Only a small amount of laboratory equipment is required for using the method or the testing unit. The reason for this is that the testing unit is configured in such a manner that it is possible to produce a nutrient medium without laboratory equipment when the testing unit is used.

If it is the case that, after the sterilization process which is assumed to have been carried out correctly or the correct implementation of which has been tested by means of the test microbe indicators described above, contamination of the matrix unit by entry of microbes into the sterilization packaging unit and settlement on the matrix unit have taken place, the microbes have been cultivated as described above. If microbes have been found multiplying on the matrix unit then this is clear evidence that microbes have entered the sterilization packaging unit after the sterilization process. This may be attributable to the fact that the sterilization packaging unit has basic faults or it may also be attributable to the fact that the ambient conditions, such as the microbial content of the air and humidity, were very unfavorable in relation to the avoidance of recontamination.

In particular, the testing unit can be inserted instead of the objects to be sterilized into the sterilization packaging unit. This type of sterilization packaging unit could be part of a batch of sterilization objects to be sterilized. After typical storage of the batch of sterilized objects, the above-described test could then be carried out, wherein the result of the test can be applied to the entire batch of sterilized objects. This ensures a particular level of quality assurance. This type of verification could be particularly practical if the expiry date given to ensure sterility has expired, but the sterilized objects are of very high value and re-sterilization is costly and difficult. After the packaged sterilized objects are handled, which is relatively risky in relation to possible recontamination, it is possible to perform a test of this type.

Furthermore, the method in accordance with the invention is preferably suitable for performing a basic test of a sterilization packaging unit. In particular, with this type of application of the method in accordance with the invention, the ambient conditions and the period of storage of the sterilization packaging unit can be predetermined.

The testing unit used can be one of the embodiments of the testing unit which are described above.

Where appropriate, it may also be practical prior to the sterilization process to load a sterilization packaging unit, which is to be tested, with objects to be sterilized in addition to the testing unit. This can ensure a high level of reliability in avoiding unrecognised recontamination of the sterilized objects.

BRIEF DESCRIPTION OF THE DRAWINGS

The invention will be explained in detail hereinunder with reference to an exemplified embodiment, wherein reference is made to the Figures, in which FIG. 1 schematically shows a perspective view of a testing unit for testing a sterilization packaging unit with regard to the barrier efficacy of the sterilization packaging unit against recontamination and FIG. 2 schematically shows a container package with a testing unit.

DETAILED DESCRIPTION OF THE EMBODIMENTS

Figure 1:
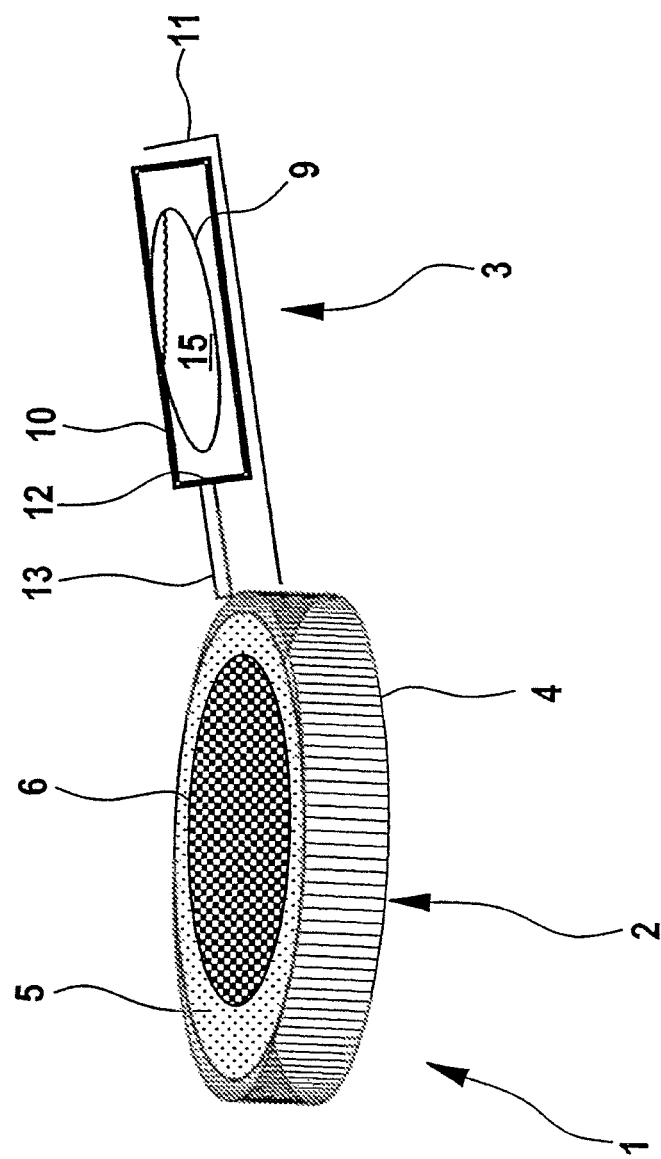

The testing unit as shown in FIG. 1 is designated by the reference numeral 1. The testing unit 1 consists of two partial elements 2 and 3. The partial element 2 comprises a thermostable solid nutrient medium dish 4. Located in the solid nutrient medium dish 4 is a nutrient board disc 5. A membrane filter 6 is secured on the nutrient board disc 5. It is secured by means of an adhesive, not shown, which is provided in the edge region of the membrane filter.

The partial element 3 comprises a glass ampoule 9. The ampoule 9 is located in a plastics casing 10. The ampoule 9 and the plastics casing 10 are disposed on a carrier 11 consisting of a suitable material which is attached to the side of the partial element 2 at an inclination with respect thereto.

The plastics casing 10 comprises an outlet 12. The outlet 12 issues into a channel 13 which extends between the plastics casing 10 and the solid nutrient medium dish 4. The ampoule 9 contains water 15.

Pressure exerted upon the plastics casing 10 and thus upon the ampoule 9 can destroy the ampoule, whereby the water 15 passes through the outlet 12 of the plastics casing 10 into the channel 13. By reason of the inclination of the partial element 3, the water 15 flows on to the nutrient board disc 5 in the solid nutrient medium dish 4. By wetting the nutrient board disc 5 with the water 15, said disc becomes a ready-to-use solid nutrient medium, on which microbes are fundamentally able to grow. The nutrient board disc 5 and the membrane filter 6, on which possible microbes settle and multiply can be selected according to specific requirements.

Figure 2:
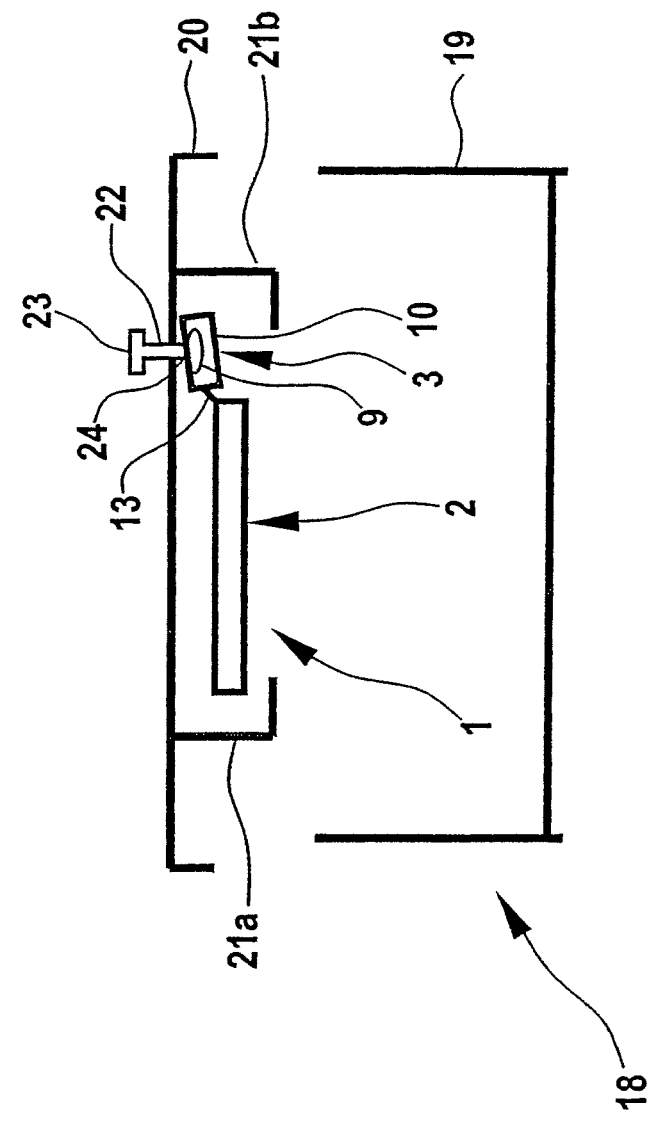

The container package as shown in FIG. 2 is designated by the reference numeral 18 and comprises a body 19 and a cover 20. The cover 20 is illustrated in a condition where it is lifted off from the body 19 and can be placed in a microbe-tight manner on to the body 19 in order to close the container package 18. A testing unit 1 is attached to the inner side of the cover 20 by means of a holder having two schematically illustrated holding elements 21a and 21b. The testing unit 1 corresponds substantially to the testing unit as shown in FIG. 1. Like parts are designated in the Figures by like reference numerals.

Through the cover 20, a threaded bolt 22 of a screw 23 is attached by means of a thread, not shown, in the cover 20 such that when the screw 23 is screwed in correspondingly to a significant extent the bolt 22 presses with its free end, which is designated as a stop portion 24, on to the plastics casing 10 of the testing unit 1 and on to the glass ampoule 9. By means of the screw 23, the glass ampoule 9 can be destroyed and it can be ensured that any water 15 contained in the glass ampoule 9 runs through the channel 13 into the partial element 2 and thus on to a nutrient board disc 5, not shown in FIG. 2.

By means of the screw 23 which could also be replaced by a corresponding similar actuating means, the ampoule 9 can thus be destroyed, if the container package 18 is closed.

What is claimed is:

1. A method of testing a sterilization packaging unit provided for the sterilization of objects with regard to the efficacy of the sterilization packaging unit in preventing microbial recontamination of the sterilized objects after they have been sterilized, said method comprising:
    inserting within said packaging unit a test unit, permeable to microbes, said test unit comprising a dry matrix adapted to support a complete nutrient medium and a sealed receptacle containing a liquid, said receptacle being operatively associated with said dry matrix;
    sterilizing said packaging unit;
    storing said packaging unit for a time period under ambient conditions;
    opening said receptacle without opening the packaging unit and thereby allowing said liquid to contact said matrix, the combination of said liquid and said matrix providing said complete nutrient medium capable of supporting microbial reproduction on said matrix;
    subjecting said packaging unit to conditions favorable for cultivation of microbes present on said matrix; and
    observing microbes which have multiplied on said matrix.

2. The method according to claim 1, wherein said receptacle comprises an ampoule.

3. The method according to claim 1, wherein said ambient conditions and said time period are predetermined.

4. The method according to claim 1, further comprising loading said packaging unit with objects to be sterilized.

5. The method according to claim 1, wherein said testing unit is inserted within said packaging unit in the absence of objects to be sterilized, wherein said packaging unit is sterilized and stored as part of a batch of sterilization objects and wherein the result of the testing is applied to the entire batch of sterilized objects.

* * * * *